(12) United States Patent
Günzburg et al.

(10) Patent No.: US 6,656,727 B2
(45) Date of Patent: Dec. 2, 2003

(54) TARGETED INTEGRATION INTO CHROMOSOMES USING RETROVIRAL VECTORS

(75) Inventors: Walter H. Günzburg, Mödling (AT); Brian Salmons, Ainhofen (AT); Sabine Goller, Vienna (AT); Dieter Klein, Tulln (AT)

(73) Assignee: Institut Fur Virologie, Vienna (AT)

( * ) Notice: Subject to any disclaimer, the term of this patent is extended or adjusted under 35 U.S.C. 154(b) by 0 days.

(21) Appl. No.: 09/752,110

(22) Filed: Dec. 29, 2000

(65) Prior Publication Data

US 2001/0043921 A1 Nov. 22, 2001

Related U.S. Application Data

(63) Continuation-in-part of application No. PCT/EP99/04521, filed on Jun. 30, 1999.

(30) Foreign Application Priority Data

Jul. 1, 1998 (DK) .......................................... 1998 01016

(51) Int. Cl.[7] .................. C12N 15/74; C12N 15/09; C12N 15/86; A61K 31/70
(52) U.S. Cl. ................ 435/320.1; 514/44; 435/455; 435/456
(58) Field of Search ................ 435/320.1; 514/44

(56) References Cited

U.S. PATENT DOCUMENTS

| | | | |
|---|---|---|---|
| 5,650,309 A | 7/1997 | Wong-Staal et al. | 435/172.3 |
| 5,856,152 A | 1/1999 | Wilson et al. | 435/172.3 |
| 5,871,982 A | 2/1999 | Wilson et al. | 435/172.3 |
| 6,063,627 A * | 5/2000 | McVey et al. | |
| 6,251,677 B1 * | 6/2001 | Wilson et al. | |

FOREIGN PATENT DOCUMENTS

| | | |
|---|---|---|
| WO | WO 96/13598 | 5/1996 |
| WO | WO 96/36705 | 11/1996 |
| WO | WO 98/42856 | 10/1998 |

OTHER PUBLICATIONS

Savvas et al. Components of vectors for gene transfer and expression in mammalian cells pp. 183–202 1999.*

Zink et al. Mammalian genome organization and its implications for the development of gene therapy vectors vol. 6, pp. 1–24 Jan. 2001.*

Verma et al. Gene therapy promises, problems and prospects vol. 389,Sep. 18, 1997 pp. 239–242.*

Johnston, Karen M. et al., 1997, "HSV/AAV Hybrid Amplicon Vectors Extend Transgene Expression in Human Glioma Cells", *Human Gene Therapy,* vol. 8, pp. 359–370.

* cited by examiner

*Primary Examiner*—Anne M. Wehbe'
*Assistant Examiner*—Qian J Li
(74) *Attorney, Agent, or Firm*—Baker Botts L.L.P.

(57) ABSTRACT

The present invention relates to a retroviral vector encoding heterologous genes particularly for gene therapy of genetic defects or viral infections.

5 Claims, No Drawings

TARGETED INTEGRATION INTO CHROMOSOMES USING RETROVIRAL VECTORS

RELATED APPLICATION(S)

This application is a continuation-in-part of International Application No. PCT/EP99/04521, which designated the United States and was filed on Jun. 30, 1999, published in English, which claims priority to Danish patent application PA 1998 01016 filed Jul. 1, 1998. The entire teachings of the above application(s) are incorporated herein by reference.

BACKGROUND OF THE INVENTION

Retroviruses infect a wide variety of cells and are ideal tools for the delivery of genes to target cells. They are furthermore an ideal tool to stably integrate a heterologous sequence in the genome of a target cell, since the infecting retrovirus is able to integrate the DNA form of its RNA genome into the genome of the target cell. Thus, all daughter cells of a retroviral infected cell carry the retroviral vector DNA possibly comprising a heterologous gene.

A retroviral genome consists of a RNA molecule with the structure R-U5-gag-pol-env-U3-R. For the development of a retroviral vector (RV) said retroviral genome can be modified by replacing the genes gag-pol-env-encoding viral proteins—with one or more genes of interest such as marker genes or therapeutic genes. To generate a recombinant retroviral particle and a packaged RV, respectively, the principle of a retroviral vector system is used. This system consists of two components: the RV itself in which the genes encoding the viral proteins have been replaced, and a packaging cell which provides the modified RV with the missing viral proteins. This packaging cell has been transfected with one or more plasmids carrying the genes enabling the modified RV to be packaged, but lacks the ability to produce replication competent viruses.

After introduction of the vector into the packaging cell line, the RV is transcribed into RNA. This RNA which represents the recombinant retroviral genome is packaged by the viral proteins produced by the packaging cell to form retroviral particles which bud from the packaging cell. These particles are further used to infect a target cell. In the target cell the RNA genome is released again from the particle, reverse transcribed and stably integrated into the cellular genome.

Therefore, RVs are currently the method of choice for a stable transfer of therapeutic genes into a target cell in a variety of approved protocols both in the USA and in Europe. However, most of the protocols require that the infecting of target cells with the RV carrying the therapeutic gene occurs in vitro. Subsequently, successful infected cells are returned to the affected individual. Advantageously, such ex vivo infection of target cells allows the administration of large quantities of concentrated virus which can be rigorously safety tested before use. Furthermore, the ex vivo gene therapy protocols are ideal for correction of medical conditions in which the target cell population can be easily isolated.

Unfortunately, only a fraction of the possible applications for gene therapy involve target cells that can be easily isolated cultured and then reintroduced to a patient. Additionally, the complex technology and associated high costs of ex vivo gene therapy effectively preclude its disseminated use world-wide. Future facile and cost-effective gene therapy will require an in vivo approach in which the RV, or cells producing the RV, are directly administered to the patient in the form of an injection or simple implantation of RV producing cells.

This kind of in vivo approach, of course, introduces a variety of new problems. First of all safety considerations have to be addressed. One serious safety risk is that virus will be produced, possibly form an implantation of virus producing cells. Thus, there will be no opportunity to precheck said produced virus. Another problem is that the proviral form of the retroviral genome integrates randomly in the genome of infected cells. This random integration can result in an integration directly into a cellular gene or into the vicinity of a cellular gene, leading to new genomic arrangements. As a result of this function of the cellular gene can be altered or lost. In the case that the cellular gene is involved in the regulation of growth control, uncontrolled proliferation of the cell may result. Therefore, using RV in gene therapeutic applications there is a potential risk that simultaneously to the repair of one genetic defect with retroviral vectors, a second defect can be established resulting in uncontrolled proliferation, and thus, in tumor development.

SUMMARY OF THE INVENTION

It is therefore an object of the invention to provide a safe retroviral vector which prevents random integration of the recombinant viral genome into genes or into the vicinity of genes of a target cell genome, thus, preventing genomic rearrangements of the target cell genome.

The invention inter alia comprises the following, alone or in combination:

A retroviral vector comprising one or more heterologous nucleic acid sequence(s) as well as at least one sequence allowing site-specific integration of said heterologous sequence(s) into a non-coding region of a genome;

the retroviral vector as above, wherein the sequence(s) allowing site specific integration is inserted at the U3 region(s) and/or the U5 region(s) of the retroviral Long Terminal Repeat (LTR);

the retroviral vector as above, wherein the sequence allowing site specific integration is an Inverted Terminal Repeat (ITR) sequence of Adeno-associated virus (AAV); the retroviral vector as any above, wherein the genome is a chromosome of a mammal, including human;

the retroviral vector as above, wherein the chromosome is chromosome 19;

the retroviral vector as any above, wherein at least one of the heterologous nucleic acid sequence(s) is a heterologous gene relevant for the treatment of a viral infection or the treatment of a genetic, metabolic, proliferative or any other relevant disorder or disease;

the retroviral vector as any above, wherein at least one of the heterologous nucleic acid sequence(s) is a sequence encoding an integration-mediating protein;

the retroviral vector as above, wherein the integration-mediating protein is the AAV Rep protein;

the retroviral vector as above, wherein the sequence encoding for the integration-mediating protein is under transcriptional control of an inducible promoter;

a retroviral vector system comprising the vector as any above as a first component, and a packaging cell harboring at least one DNA construct encoding for proteins required for said vector to be packaged;

the retroviral vector system as above, wherein the packaging cell synthesizes a mutated or a completely or partially deleted retroviral integrase (IN);

a retroviral particle comprising a retroviral vector as any above;

the retroviral particle as above obtainable by transfecting a packaging cell of a retroviral vector system as above with the retroviral vector as above;

a retroviral provirus produced by infection of target cells with the retroviral particle as above;

mRNA of a retroviral provirus as above;

RNA of the retroviral vector as any above;

cDNA of the RNA as above;

a host cell infected with the retroviral particles as above;

a method for introducing homologous and/or heterologous nucleotide sequences into target cells comprising infecting the target cells with retroviral particles as above;

the retroviral vector as any above and/or the retroviral particle as above and/or the retroviral vector system as above for the use in the treatment of a viral infection or the treatment of a genetic, metabolic, proliferative or any other relevant disorder or disease;

use of the retroviral vector as any above and/or the retroviral particle as above and/or the retroviral vector system as above for producing a pharmaceutical composition for the treatment of a viral infection or the treatment of a genetic, metabolic, proliferative or any other relevant disorder or disease;

a pharmaceutical composition containing a therapeutically effective amount of the retroviral vector as any above and/or the retroviral particle as above and/or the retroviral vector system as above;

a method of treating a viral infection or a genetic, metabolic, proliferative or any other relevant disorder or disease comprising administering to a subject in need thereof a therapeutically effective amount of the retroviral particle as above and/or the retroviral vector system as above.

DETAILED DESCRIPTION OF THE INVENTION

The basic idea underlying the present invention is the provision of a recombinant retroviral vector which specifically integrates into a targeted region of a target cell genome. Thus, to achieve the foregoing and other objects, the present invention provides a retroviral vector (RV) comprising at least one integration-mediating sequence, wherein said sequence is site-specific for a targeted region of a target cell genome. The sequence is, thus, included into the recombinant retroviral genome, preferably within the retrovirus-derived sequences, and is transferred into a target cell. For transfer, the retroviral vector is preferably packaged into a retroviral particle. After transfer into the target cell the retroviral vector is integrated into a specific site of the target cell genome, whereby said specific site is determined by the site specific integration-mediating sequence included in the vector.

The term "site specific" integration-mediating sequence includes that the sequence is of non-retroviral origin. Integration-mediating sequences of retroviral origin are generally non-site-specific and do, thus, only allow random integration into the genome of the target cell. The inventors of the present invention showed for the first time that retroviral sequences can be integrated into a target cell by non-retroviral sequences. Integration-mediating sequences, specifically those of non-retroviral origin, are known to form stable secondary structures, as, e.g., "hairpin loop" structures, which are generally inaccessible for enzymes. Such structures may, thus, inhibit enzyme activities. When now considering the life cycle of a retrovirus, it was not awaited that a non-retroviral integration-mediating sequence would mediate integration of the retroviral genome into the target cell genome:

When a retroviral genome has entered a target cell, the retroviral RNA is reverse transcribed into DNA and, subsequently, the DNA is integrated into the host cell genome. The integrated DNA is further transcribed into mRNA, wherein transcription starts at the U5-region of the 5'-LTR and ends at the U3-region of the 3'-LTR. When the integration-mediating sequence is included in the retroviral vector, the integration-mediating sequence must also be reverse-transcribed, must be integrated into the target cell genome and, subsequently, must be transcribed into the mRNA. However, reverse transcription, integration and transcription of the DNA into RNA are all dependent on catalytic functions of specific enzymes. Said catalytic functions can only develop after binding of the enzymes to the nucleic acid sequence. As mentioned above, non-retroviral integration-mediating sequences form secondary structures, which may hinder enzymes to bind to the nucleotide sequence. Accordingly, the skilled practitioner would have at first expected that the insertion of integration-mediating sequences into a retroviral vector would result in the formation of secondary structures, preventing binding of the enzyme catalyzing reverse transcription and thereby inhibiting reverse transcription. Even if it was awaited that reverse transcription would take place, the inhibition of the integration would have been further expected also due to the secondary structures of the integration-mediating sequences. However, without reverse transcription and integration of the retroviral vector the retroviral sequence is not stable. Hence, it was expected that the retroviral vector including a non-retroviral integration-mediating sequence would be lost shortly after it enters the target cell.

However, only assuming, it could be awaited that the retroviral vector would integrate into the target cell genome, the skilled practitioner would further not have expected that the integrated sequence would be transcribed and translated. More likely, the skilled practitioner would have expected that the large transcription complex necessary for transcription of the integrated DNA could not bind to the nucleic acid sequence again due to the secondary structures of the non-retroviral sequence and additionally due to the large size of the enzyme complex. Consequently, no synthesis of mRNA of the retroviral part included in the host cell genome was expected. Furthermore, since transcription of said mRNA starts at the retroviral promoter in the 5'-LTR, the mRNA also comprises the integration-mediating sequence. Hence, the mRNA was expected to again form secondary structures. Accordingly, it was further expected that the large translation complex could not anneal to the mRNA, resulting in no translation of the mRNA into protein. Accordingly, even if integration of the retroviral vector into the target cell genome was expected, the skilled practitioner would not have expected that protein encoded by sequences integrated into the retroviral vector would be produced. However, in contrast to all the above expectations, it was found that the retroviral vector according to the present invention is not only reverse transcribed and integrated, but that also proteins are produced from the sequence inserted into the vector.

Preferably, the integration-mediating sequence included in the retroviral vector is specific for a non-coding region of the target cell genome, i.e., due to the sequence allowing site-specific integration the RV interacts with a genomic region which does not contain any coding or regulatory sequences. Interaction and subsequent integration may occur by homologous recombination or to another, e.g. protein mediated, integration mechanism. Generally, the retroviral integration process is mediated by an integration-mediating enzyme, which is comprised in an infectious retroviral particle. The integration-mediating protein interacts with the sequence allowing site-specific integration encoded by the RV as well as with the site of integration within the region of the genomic sequence of the target cell. Thus, said target cell is infected by a retroviral particle comprising the RV and optionally an integration-mediating protein. Consequently, site-specific integration of the RV into a genomic region of a target cell occurs.

As a result of site-specific integration of the RV the risk of new genomic arrangements, e.g. leading to disregulations of gene products or uncontrolled cellular proliferation, is avoided. Thus, the RV according to the present invention is highly adapted for future in vivo, but also in vitro transfer of heterologous nucleic acid sequences to target cells of mammals, including humans. Thus, according to a further preferred embodiment of the present invention the vector additionally includes one or more heterologous nucleic acid sequence(s).

The term "heterologous" is used for any combination of DNA sequences that is not normally found intimately associated in nature. Accordingly, at least one of the heterologous nucleic acid sequences of RV as described above is a heterologous gene relevant for the treatment of a viral infection, a genetic, a metabolic, a proliferative or any other relevant disorder or disease. Therefore, heterologous genes which can be transferred to target cells by the RV according to the present invention are preferably, but not limited to one or more elements of the group consisting of marker genes, therapeutic genes, antiviral genes, antitumor genes, cytokine genes and/or toxin genes. The marker and therapeutic genes are preferably selected from genes such as β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene, hypoxanthine phosphoribosyl transferase (HPRT) gene, green fluorescent protein (gfp) gene, cytochrome P450 gene and/or toxin genes such as a subunit of diphtheria, pertussis toxin, tetanus toxoid.

To ensure that during the integration event the heterologous sequence(s) encoded by the RV integrates into a genomic non-coding region, said heterologous sequence(s) is flanked by one or more sequences allowing site-specific integration. Generally, it is possible to introduce the process of integration with a single copy of the sequence allowing site-specific integration, which in this case flanks only one end of the heterologous sequence to be integrated. However, in a preferred embodiment the sequences allowing site-specific integration flank—directly or at some distance— both sites of the heterologous sequences to be integrated. Thus, said sequences allowing site-specific integration are preferably inserted into the U3 region(s) and/or U5 region(s) of the retroviral LTR. Alternatively, said sequences allowing site-specific integration could be inserted joining the heterologous sequence to be integrated. In this case, only the heterologous sequence to be integrated without any further retroviral sequences will be site-specifically integrated. Therefore, in this case the RV serves only as a vehicle for the transport of the heterologous sequences to be integrated into the target cell.

The RV according to the present invention is particularly useful for the site specific integration into a non-coding region of a mammalian, including a human chromosome, since it is known that more than 90% of the mammalian genome consist of non-coding regions. In a further embodiment of the present invention the RV integrates specifically in a non-coding region, which is located on human chromosome 19. Said specific non-coding DNA region on human chromosome 19 was first described as the target site for the integration of Adeno-associated virus (AAV). For an integration into said non-coding region on chromosome 19, in still a further embodiment of the present invention, the sequences allowing site-specific integration of the RV are the so called Inverted Terminal Repeats (ITRs) of the AAV.

When combining these features of phylogenetic different viruses it was found as particularly advantageous that the resulting RV according to the present invention, can still accommodate a capacity of about 8 kb of heterologous DNA sequences, which can be targeted to a non-coding region in the genome. In comparison, all existing AAV based vectors can accommodate a maximum of about 4,5 kb of heterologous DNA in the presence of all coding region required for targeted integration into chromosome 19 (Dong et al., 1996, "Quantitative analysis of the packaging capacity of recombinant adeno-associated virus," Hum. Gene Ther., 7(17): 2101–2112)). Unfortunately, this is too little to be of practical use for most gene therapies.

The present invention also provides a method for introducing a homologous or heterologous nucleic acid sequence into the genome of a target cell. According to this method, said sequence is included into a retroviral vector and transferred by this vector into the target cell—by transfection and/or infection with a retroviral particle including said vector. However, integration of said sequence into the target cell genome is catalyzed by a non-retroviral integration-mediating protein. It was surprisingly found that a non-retroviral integration-mediating protein can indeed mediate integration of sequences included in a retroviral vector. At the time the invention was made integration of vectors derived from, e.g., DNA viruses was only mediated by proteins also derived from a DNA virus, i.e. it was only common practice that for integration of vectors from a DNA organism the integration-mediating protein must also be derived from the same origin, namely from a DNA organism. Accordingly, for integration of a retroviral vector derived from an RNA genome and a retrovirus, respectively, only retroviral integrase was used. However, it was not expected that sequences included in a retroviral vector can be integrated by a non-retroviral integration-mediating protein.

In a preferred embodiment of the present invention the AAV-Rep protein is used for the site-specific integration of the RV. It was surprisingly found that the AAV integration-mediating Rep Protein can be used for targeted integration of the RV into the same non coding region of the chromosome 19 which this protein normally uses for the AAV integration process. As already indicated above, this was particularly unexpected, since a RV is based on a virus with RNA genome, while AAV belongs to the viruses with a DNA genome. According to these differences in genome structure also the regulation or integration mechanism is completely different. Whereas the integration of the retroviral genome is normally dependent on the enzyme integrase (IN), the site-specific integration of the AAV genome is mediated by the Rep protein. Since this protein is AAV-specific it was not expected that the integration of a foreign genome would be mediated by this protein. Additionally, it was not expected that a protein of a DNA virus—belonging to a completely different phylogenetic group when combined with a RNA virus—would mediate integration of a retroviral genome.

To provide a target cell with an integration-mediating protein, e.g. said AAV-Rep protein, one alternative is to directly incorporate the nucleic acid sequence encoding said protein in the RV. After infection of a target cell with the RV the integration-mediating protein, e.g. the AAV Rep protein, is directly synthesized in the target cell. Subsequently, the AAV Rep protein mediates site-specific integration of the RV.

Alternatively, the packaging cell provides the retroviral particle (RVP) with the integration-mediating protein, e.g. AAV Rep protein. In this case the integration-mediating protein is synthesized from the packaging cell and packaged into newly generated infectious retroviral particles (RVP). Subsequently, these particles are used to infect a target cell, and thereby, transfer said additional integration-mediating protein together with the RV into the target cell.

It is known that the expression of an integration-mediating protein, particularly of the AAV Rep protein, induces at higher concentrations toxic effects in cells. Accordingly, in a further embodiment of the present invention the expression of the integration-mediating protein as well as of the AAV Rep protein is under the transcriptional control of an inducible and/or a very weak promoter. The inducible promoters and/or very weak promoters are selected preferably, but not limited, from one or more elements of the group consisting of promoters inducible by Tetracycline, promoters inducible by HIV Tat transactivator, promoters inducible by glucocorticoid hormones, such as the MMTV promoters or promoters inducible by X-ray.

For the generation of RVP in a further embodiment of the invention a retroviral vector system is provided, which comprises the RV as described above as a first component and a packaging cell providing the proteins required for the RV to be packaged. The packaging cell line is selected preferable but not limited, from an element of the group consisting of psi-2, psi-Crypt, psi-AM, GP+E-86, PA317, GP+envAM-12, Fly A13, BOSC 23, BING, Fly RD 18, ProPak-X, -A.52 and -A.6, or of any of these supertransfected with recombinant constructs allowing expression of surface proteins from other enveloped viruses.

To ensure a high efficacy of site-specific integration of the RV the packaging cell according to a further embodiment of the present invention provides a Gag/Pol expression plasmid that does not encode a functional retroviral integrase (IN). Accordingly, the packaging cell is constructed in such a way that no functional retroviral IN which is encoded by the pol-region can be synthesized. For this, the packaging cell is generated using a DNA construct encoding a retroviral pol-region which incorporates mutations and/or partial or complete deletions of the pol-region. To introduce mutations or deletions in the pol-region leading to a non-functional IN preferably recombinant PCR technology is used.

The invention further provides retroviral particles comprising the RV of the invention as described above. These particles can be obtained by transfecting according to standard protocols the packaging cell as described above with RV as described above.

The invention includes a retroviral provirus, mRNA of a retroviral provirus according to the invention, any RNA resulting from a retroviral vector according to the invention and cDNA thereof, as well as target cells infected with a retroviral particle according to the invention.

A further embodiment of the invention provides a method for introducing homologous and/or heterologous nucleotide sequences into target cells comprising infecting a target cell population in vivo and in vitro with recombinant retroviral particles as described above. Furthermore, the retroviral vector, the retroviral particle, the retroviral vector system and the retroviral provirus as well as RNA thereof is used in the treatment of a viral infection or the treatment of a genetic, metabolic, proliferative or any other relevant disorder or disease.

The retroviral vector, the retroviral particle, the retroviral vector system and the retroviral provirus as well as RNA thereof is used for producing a pharmaceutical composition for in vivo and in vitro gene therapy in mammals including humans.

The invention further includes a method of treating a viral infection or a genetic, metabolic, proliferative or any other relevant disorder or disease comprising administering to a person in need thereof a therapeutically effective amount of the retroviral particle and/or the retroviral vector system and/or a pharmaceutical composition containing a therapeutically effective amount of the retroviral vector, vector system or particle.

EXAMPLES

The following examples will further illustrate the present invention. It will be well understood by any person skilled in the art that the provided examples in no way should be interpreted in a limiting manner and that the invention is only to be limited by the full scope of the appended claims.

Example 1

Targeted Integration of a RV
1. Construction of a Retroviral Vector (Rv) Containing the Inverted Terminal Repeat (ITR) Motif of the AAV Genome The RV vector pLESN1IP was constructed by litigation of the fragment containing the ITR sequence obtained from plasmid pAVI (Laughlin et al., 1983, *Cloning of infectious adeno-associated virus genomes in bacterial plasmids*. Gene 23: 65–73) and the backbone sequence of the RV vector pLESNMP (identical to pLXSNPCEGPF of Klein et al. (1997) Gene Therapy 4: 1256–1260).

For this, the plasmid, pLESNMP, was digested with the restriction enzymes SacII and MluI eliminating the MMTV U3 region and yielding in a 7065 bp fragment. The digestion mixture was purified on a 0.8% agarose gel, the DNA band was excised and eluted using the Qiaquick protocol (Qiagen). After ethanol precipitation the DNA was resuspended in water.

The ITR sequence was isolated from the plasmid pAV1 using the PCR method. Therefore, the left hand primer(5'-GACTCC<u>ACGCGT</u>CCAGGAAC-3') (SeqID No. 1) was specific to the beginning of the ITR also creating a new MluI restriction site (underlined) and the right hand primer (5'-GACCGCGGATCATCGATAAG-3') (SeqID No. 2) end of the ITR also creating a SacII restriction site (underlined). PCR resulted in a 198 bp fragment, which was digested with the restriction enzyme MluI and SacII and subsequently, purified.

50 ng of the prepared pLESNMP backbone fragment and 300–400 ng of the MluI/SacII digested PCR fragment were mixed together. For ligation the temperature was increased for 1° C. per hour from 10° C. to 22° C. using the NEB ligase (New England Biolabs). The ligase was inactivated at 65° C. for 10 min and DNA transfected into chemically competent TOP10 bacteria (Invitrogen). Ampicillin resistant colonies were selected, DNA prepared and test digested with the restriction enzyme HindIII. The final correct plasmid was designated pLESN1IP.

2. Construction of Two RV Containing Two ITR Motifs of the AAV Genome

The RV pLESN2IP and pLESN2IP6, which differ only in location of a restriction site, were constructed by litigation of the fragment containing the ITR obtained from plasmid pAV1 and the ProCon vector pLESN1IP backbone of item 1.

The pLESN1IP backbone was digested with the restriction enzyme AgeI linearizing the vector. The digested DNA was dephosphorylated with alkaline phosphatase (Boehringer). After phenol and chloroform extraction the DNA was ethanol precipitated and resuspended in water.

The ITR motif was isolated from the plasmid pAV1 using the PCR method as described under item 1, but with a different primer combination. In this case the left hand primer(5'-TCACGACTCCACCGGTCCAGGAAC-3') (SeqID No.: 3) was specific to the beginning fo the ITR also creating a new AgeI restriction site (underlined) and the right hand primer (5-GTTTG ACCGGTTATCATCGATAAG-3') (SeqID No.: 4) was specific to the end of the ITR also creating a new AgeI restriction site (underlined). PCR resulted in a 206 bp fragment, which was digested with the restriction enzyme AgeI and purified.

50 ng of the linearized pLESN1IP backbone and 300–400 ng of the AgeI digested PCR fragment were mixed together, ligated and transfected to bacteria as described under item 1. Ampicillin resistant colonies were selected, DNA prepared and test digested with the restriction enzymes EcoRI and HindIII. The final correct RV were designated pLESN2IP1 and pLESN2IP6.

3. Production of Retroviral Particles (RVP) using the RV pLESN1IP, pLESN2IP1, or pLESN2IP6

For the transfection of the packaging cell lines $5 \times 10^5$ cells (e.g. PA317) were seeded into 6-well dishes with a diameter of 35 mm. At the day of transfection 10 $\mu$g of pLESN1IP, pLESN2IP1 and pLESN2IP6 were transfected using the calcium-phosphate protocol Cellfect Kit (Pharmacia) according to the manufacturer's instructions.

18 h post transfection the medium was changed. After another 24 h the medium containing RVPs was removed and used for infection of target cells. Additionally, new medium containing G418-Geneticin was added to transfected packaging cells to select for stably transfected cells.

4. Infection of Target Cells with RVPs Containing RV with One or Two ITR Motifs for Targeted Integration into Chromosomes For the infection of target cells (e.g. HeLa; NIH3T3) $2 \times 10^6$ cells in 10 ml medium were seeded in culture dishes with a diameter of 10 cm. At the day of infection, 2 ml of sterile filtered supernatant containing vector virus and 2 $\mu$l Polybrene (final concentration 8 $\mu$g/ml) were added to the cells. After 6 h fresh culture medium was added to the cells. 24 h post infection new medium containing G418-Geneticin was added to select for stably infected cells. To test for targeted integration into a non-coding region on a chromosome the cellular genomic DNA was isolated and analyzed in a Southern blot. Several clones have been identified that showed homogenous integration pattern. To further identify the integration locus a FISH-Chromosome assay was performed on said clones.

Example 2

Targeted Integration of a RV using the AAV Rep Protein

1. Production of RVP Containing RV with One or Two ITR Motifs of AAV in a Packaging Cell Line Synthesizing the AAV Rep Protein Encoded on the Plasmid pSVoriAAV (Chiorini et al., 1995, Human Gene Therapy 6: 1531–1541)

For lipofection of packaging cell lines $2 \times 10^5$ cells (e.g. PA317) were seeded into 6-well dishes with a diameter of 35 mm. At the day of transfection 2 $\mu$g of the RV as in example 1 and 0.1–0.2 $\mu$g of pSVoriAAV encoding the rep gene were cotransfected using the Lipofectin protocol (Gibco) according to the manufacturer's instructions.

5 h post transfection the medium was changed and 48 h post transfection the medium containing RVPs was removed and used for infection of target cells. Additionally, new medium containing G418-Geneticin was added to the transfected cells to select for stably transfected cells.

Alternatively, the packaging cell line is transfected using the calcium-phosphate protocol (Cellfect Kit, Pharmacia) according to the manufacturer's instruction. In this case 10 $\mu$g of the RV as in example 1 and 0,5–1 $\mu$g of pSVoriAAv encoding the rep gene were cotransfected.

2. Infection of Target Cells with RVP as Described in Example 1 Item 4

For infection the target cells (e.g. HeLa; NIH3T3) were infected and selected according the protocol described in example 2 item 2 with RVP containing the RV and AAV Rep protein. To test for targeted integration into the non-coding region on chromosomes after selection the cellular gnome DNA was isolated, screened in a Southern blot and analyzed in a FISH-Chromosome assay.

Example 3

Construction of a Integrase Deficient Packaging Cell Line

1. Inactivation of the MLV Integrase by Single Base Pair Mutation of te pol-region The expression plasmid pGagPol.gpt (Markowitz et al. (1988) Virology 167 (2): 400–406) containing the MLV integrase gene was used for site-directed mutation. Using a polymerase chain reaction (PCR) method a site-directed mutation at amino acid 184 which is within the catalytic site of this enzyme was introduced. For this, recombinant primers were used which exchange one nucleotide (underlined) thereby replacing the aspartic acid within the catalytic site with an asparagine.

For this, in a first PCT the primer, (5'-ACA AGT CAA CGC CAG CAA GT-3') (SeqID NO.: 5) and the primer (5'-CCC ATT GTT AGT TCC CAA TAC CTG AG-3' (SeqID No. 6) comprising the nucleotide exchange from C to T (underlined) complementary to the sense DNA strain were used.

In the second PCR the primer(5'-TGG GAA CTA ACA ATG GGC CTG CCT-3') (SeqID No.: 7) comprising the nucleotide exchange from G to A (underlined) and the primer (5'-CGT TGA ACG CGC CAT GTC AG-3') (SeqID N.: 8) complementary to the anti-sense DNA strain were used. The resulting PCR fragments from both reactions were purified and subsequently used as template in a third PCR. After three initial cycles at 45° C. the temperature was increased to 55° C. and the primers (SeqID No.: 5) and (SeqID No.: 8) added. After 32 cycles the PCR fragment was purified, digested with the restriction enzymes NdeI and SacII arising a 450 bp fragment and again purified.

The plasmid pGagPol.gpt containing two NdeI restriction sites (one within and one outside the integrase gene) and one SacII restriction site (within the integrase gene) was digested with the restriction enzymes NdeI and SacII resulting in a 9467 bp NdeI/SacII vector backbone, a 2948 bp NdeI/NdeI and a 450 bp NdeI/SacII DNA fragment. The backbone fragment was isolated and purified.

20 ng of the pGagPol.gpt backbone and 20 ng of the mutated NdeI/SacII PCR fragment, respectively, were mixed together and ligated for 12 h at 4° C. using T4-ligase (Boehringer). The ligase was inactivated at 65° C. for 20 min and the DNA butanol precipitated with a 10 fold volume of butanol. The precipitated DNA was resuspended in water and electroporated into DH10B bacteria (Gibco). Ampicillin resistant colonies were selected, DNA prepared and test digested with the restriction enzymes XhoI and NdeI. Additional verification was obtained by sequencing resulting plasmids. The intermediate correct plasmid was designated pIN1-264new.

In the intermediate plasmid pIN1-264new one NdeI restriction site was lost. In order to recover the missing 2948 bp NdeI/NdeI fragment, pIN1-264new was digested with the restriction enzymes XhoI and NdeI resulting in a 3842 bp and a 6075 bp fragment (digest 1). The expression vector pGagPol.gpt was also digested with the restriction enzymes XhoI and NdeI resulting in a 2948 bp, a 3842 bp and a 6075 bp fragment (digest 2). All DNA fragments were purified. Subsequently, 40 ng of the 3842 bp NdeI/XhoI fragment of digest 1 and 30 ng of the 2948 bp NdeI/NdeI and 37.5 ng of the 6075 bp NdeI/XhoI fragments of digest 2 were mixed together and ligated at a temperature from 6° C. to 16° C. increasing one degree per hour using T4 ligase (Boehringer). The ligase was inactivated at 65° C. for 20 min and the DNA butanol precipitated with a 10 fold volume of butanol. The precipitated DNA was resuspended in water and electroporated into DH10B bacteria (Gibco). Ampicillin resistant colonies were selected, DNA prepared and test digested with the restriction enzymes XhoI, NdeI and HindIII and sequenced. The final correct plasmid was designated pIND184N.

2. Inactivation of the MLV Integrase by Single Base Pair Mutation, Introduction of a Frame Shift Mutation and an Artificial Stop Codon in the pol-region As described above the expression plasmid pGagPol.gpt is used in a different PCR set up. Thus, in the first PCR the primer (SeqID No.: 5) and the primer(5'-GGC CCA TTG T TA GTT CCC AAT ACC TGA G-3') (SeqID No.: 9) comprising the nucleotide exchange from C to T (underlined) complementary to the sense DNA strain were used. For the second PCR the primer(5'-TGG GAA CTA ACA ATG GGC CCT GC-3') (SeqID No.: 10) comprising the nucleotide exchange from G to A (underlined) and an additional C (bold) as well as the primer (SeqID No.: 8) complementary to the anti-sense DNA strain were used. The nucleotide exchange introduced with this primers replaces the aspartic acid within the catalytic site with an asparagine. Further the additional C was inserted to introduce a frame shift mutation. The PCR fragments were purified and used as templates in a third PCR which was performed as described under item 1 of example 3.

The resulting fragment was digested with the restriction enzymes NdeI and SacII arising a 451 bp fragment, which was purified. Subsequently, 5 ng of the mutated NdeI/SacII PCR fragment were ligated using T4-ligase (Boehringer) to 20 ng of the pGagPol.gpt backbone as prepared under item 1 of example 3. After 18 h at 12° C. the ligase was inactivated at 65° C. for 20 min, the DNA butanol precipitated with a 10 fold volume of butanol and the precipitated DNA electroporated into DH10B bacteria (Gibco). Ampicillin resistant colonies were selected, DNA prepared and test digested with the restriction enzymes XhoI and NdeI and sequenced. The intermediate plasmid was designated pIN1-264M.

In order to recover the missing 2948 bp NdeI/NdeI fragment in the plasmid, pIN1-264M, it was digested with the restriction enzymes XhoI and NdeI resulting in a 3843 bp and a 6075 bp fragment (digest 3). The expression vector pGagPol.gpt was digested with the restriction enzymes XhoI and partially digested with NdeI resulting in a 9023 bp and a 3842 bp fragment (digest 4). The fragments from both digests were purified as described above. 20 ng of the 3843 bp NdeI/XhoI fragment of digest 3 and 26 ng of the 9023 bp NdeI/XhoI backbone of digest 4 were ligated for 18 h at 12° C. using T4 ligase (Boehringer). After purification and electroporation—as described above—ampicillin resistant colonies were selected and test digested with the restriction enzyme PmaCI. Sequence analysis confirmed successful site-directed mutation of the amino acid 184 and a correctly introduced additional C at bp 6465 leading to a frame shift from AA 187 to AA 203 followed by an artificial stop codon. The final correct plasmid was designated pIN1-203M15.

3. Inactivation of MLV Integrase by Deletion Mutagenesis of the pol-region

The expression plasmid pGagPol.gpt was used for deletion mutagenesis at the C-terminus beyond the catalytic site of the integrase. Therefore, the nine different PCR primers (Table 1, SeqID No.: 11–19) which were specific to the integrase region within the pol gene were used in several PCR combined with the primer, (5'-GTCAGCAACCAGGTGTGGAA-3') (SeqID No. 20) which is specific to the pol gene within the integrase region downstream the naturally occurring SfiI restriction site. Said primer introduce a new SfiI site (underlined) to the amplification product.

The different length of the resulting PCR amplification products using the nine different forward primers is also indicated in Table 1.

TABLE 1

| Primer | Sequence | PCR product |
|---|---|---|
| primer 263 SeqID No.: 11 | ATATAGGCCCCCATGGCCTCCCCTAATC CCCTTAATTCT | 2246 bp |
| primer 277 SeqID No.: 12 | ATATAGGCCCCCATGGCCTCCGCTCTCA AAACCCCTTAAA | 2288 bp |
| primer 289 SeqID No.: 13 | ATATAGGCCCCCATGGCCTCGGTGGACC ATCCTCTAGAC | 2324 bp |
| primer 306 SeqID No.: 14 | ATATAGGCCCCCATGGCCTCGGCATCGC AGCTTGGATAC | 2375 bp |
| primer 360 SeqID No.: 15 | ATATAGGCCCCCATGGCCTCGCAGCCTA CCAAGAACA | 2533 bp |
| primer 364 SeqID No.: 16 | ATATAGGCCCCCATGGCCTCTGGAGACCT CTGGCGGCA | 2551 bp |
| primer 371 SeqID No.: 17 | ATATAGGCCCCCATGGCCTCTTAGTCCAG CACGAAGTC | 2568 bp |
| primer 381 SeqID No.: 18 | ATATAGGCCCCCATGGCCTCTCTCTCCAA GCTCACTTA | 2598 bp |
| primer 392 SeqID No.: 19 | ATATAGGCCCCCATGGCCTCGACCCTGAC ATGACAAG | 2630 bp |

The purified amplification products were digested with the restriction enzyme SfiI and purified again. Accordingly, the cloning vector pGagPol.gpt was digested with the restriction enzyme SfiI resulting in a 10408 bp and a 2457 bp fragment. The purified 10408 bp backbone fragment was ligated to the different SfiI PCR generated fragments.

The following amount of the pGagPol.gpt backbone and SfiI PCR generated fragment was mixed for a Ligation reaction:

| PCR fragment size | pGagPol.gpt backbone | SfiI fragment |
|---|---|---|
| 2246 bp: | 3 ng | 5 ng |
| 2288 bp: | 3 ng | 7.5 ng |
| 2324 bp: | 3 ng | 5 ng |
| 2375 bp: | 4 ng | 10 ng |
| 2533 bp: | 10 ng | 60 ng |
| 2551 bp: | 50 ng | 25 ng |
| 2568 bp: | 10 ng | 30 ng |
| 2598 bp: | 10 ng | 15 ng |
| 2630 bp: | 10 ng | 45 ng |

Ligation was carried out for 14 h at 12° C. using T4-ligase (Boehringer). After inactivation, precipitation and electroporation as described above ampicillin resistant colonies were selected, test digested with the restriction enzyme NdeI and sequenced. The final plasmids representing different deletion mutations in the MLV integrase gene were designated: pIN263, pIN277, pIN289, pIN306, pIN360, pIN364, pIN371, pIN381 and pIN392.

4a. MoMLVenv Expression Vector for the Construction of a MoMLVenv Expressing Packaging Cell The expression vector pSV-Menv was constructed by ligation of the fragment containing the MoMLV env gene obtained from plasmid pGR102 (Salmone et al., (1985) Virol 144: 101–114) and the pSV2neo (Southern and Berg, 1982) backbone, respectively.

Therefore, the vector pSV2neo was digested with the restriction enzymes HindIII and BssHII. The 4831 bp backbone fragment was purified. Additionally, the MoMLV env gene was isolated from the plasmid pGR102 using the PCR method. Thus, the primer Menvf(5'-GCG AAGCTTTCCACAGGATGCCGAATCACC-3') (SeqID No.: 21) specific to the beginning of the env gene also creating a new HindIII restriction site (underlined), and the primer Menvr (5'-ATA GCGCGCCCAAGTTTGCAGCAGAGAATG-3') (SeqID No.: 22) specifics to the end of the env gene also introducing a new BssHII restriction site (underlined), were used. The amplification product resulted in a 2186 bp fragment, which was digested with the restriction enzymes HindIII/BssHII and purified again.

Subsequently, 10 ng of the pSV2neo backbone and 10 ng of the HindIII/BssHIII fragment were ligated for 12 hours at 16° C. using T4-Ligase (BRL). After ligation, electroporation, as described above, ampicillin resistant colonies were tested. The correct plasmids were designated pSV-Menv.

4b. Further MoMLVenv Expression Vector

The expression vector pMOVenv was constructed by ligation of fragments containing the MoMLVenv gene obtained from plasmid pMOV1⁻ (Mann et al. (1983) Cell 33: 153–159) and the backbone of pSV-Menv, as described under item 4a of example 3.

For this, the vectors pMOV1⁻ and pSV-Menv were digested with the restriction enzymes HindIII and BssHII yielding in a 3318 bp and a 14535 bp and a 4831 bp and a 2186 bp fragment, respectively. The 3318 bp and 4831 bp fragments were purified.

Subsequently, 50 ng of the 3318 bp HindIII/BssHII fragment of pMOV1⁻ containing the MoLVenv gene were mixed together with 60 ng of the 4831 bp pSV-Menv backbone and ligated for 12 hours at 16° C. using T4-Ligase (BRL). After litigation, electroporation, as described above, ampicillin resistant colonies tested with the restriction enzymes BamHI, ClaI, XbaI, BssHII and HindIII. The correct plasmids were designated pMOVenv.

5a. Construction of Stable Semi-packaging Cell Lines Carrying the MLV gag-pol Coding Region Including a Mutated or Partially Deleted Integrase Gene For stable transfection of cell lines $5 \times 10^5$ cells (e.g. COS 7, HT 10080, 293T, 293) were seeded into dishes with a diameter of 100 mm. On the day of transfection 10 μg of pGAGPOL.gpt, pIN184N, pIN1-203M15, pIN263, pIN277, pIN289, pIN306, pIN360, pIN364, pIN371, pIN381 or pIN392 were transfected using the calcium-phosphate protocol Cellfect Kit (Pharmacia) according to the manufacturer's instructions. 14 h post transfection medium was changed and 24 h post transfection cells were trypsinized and transferred into a 225 cm² flask and medium containing 15 μg/ml hypoxanthin, 250 μg/ml xanthin, 25 mg/ml mycophenolic acid was added to select for stably transfected cells. The stable semi-packaging cell lines were designated 29GAG, 29184, 29203, 29263, 29277, 29289, 29306, 29360, 29364, 29371, 29381 and 29392 in the case of the 293. The names for the other cell were given analogous for 293T (2TGAG-2T392), COS7 (COGAG-CO392) and HT 1080 (HTGAG-HT392).

5b. Construction of Stable Viral Vector Producing Cell Lines Carrying the MLV gag-pol Coding Region Including a Mutated or Partially Deleted Integrase Gene, the MoMLVenv Region and a MoMLV Based Viral Vector For stable transfection of cell lines $5 \times 10^5$ cells (e.g. 29GAG, 29184, 29203, 29263, 29277, 29289, 29306, 29360, 29364, 29371, 29381 and 2939) were seeded into dishes with a diameter of 100 mm. On the day of transfection 10 μg of pLXSNEGFP (Klein et al. (1997) Gene Therapy 4: 1256–1260) and 10 μg of pALF (Cosset et al (1995) J. Virol. 69: 7430–7436) were transfected using the calcium-phosphate protocol Cellfect Kit (Pharmacia) according to the manufacturer's instructions. 14 h post transfection medium was changed and 24 h post transfection cells were trypsinized and transferred into a 225 cm² flask and medium containing 50 μg/ml phlemoycin was added to select for stably transfected cells. After this initial selection for two weeks the medium was changed into medium containing 400 μg/mg G418 for an additional two weeks of selection. The populations were named 29GAGVPC, 29184VPC, 29203VPC, 29263VPC, 29277VPC, 29289VPC, 29306VPC, 29360VPC, 29364VPC, 29371VPC and 29392VPC.

5c. Construction of Transiently Viral Vector Producing Cell Lines Carrying the MLV gag-pol Coding Region Including a Mutated or Partially Deleted Integrase Gene, the VSV G Protein Gene and a MLV Based Viral Vector For stable transfection of cell lines $5 \times 10^5$ cells (e.g. 29GAG, 29184, 29203, 29263, 29277, 29289, 29306, 29360, 29364, 29371, 29381 and 2939) were seeded into dishes with a diameter of 100 mm. On the day of transfection 10 μg of pLXSNEGFP (Klein et al. (1997) Gene Therapy 4:1256–1260) and 10 μg of pHCMV-G (Burns et al. (1993) Proc. Natl. Acad. Sci USA 90: 8033–8037) were transfected using the calcium-phosphate protocol Cellfect Kit (Pharmacia) according to the manufacturer's instructions. 14 h post transfection medium was changed and 24 h post transfection supernatant from cells were collected.

6. Analysis of the Influence of Integrase Mutations

The influence of mutations in the pol region on reverse transcription and integration of the retroviral genome was studied. Retroviral particles produced by the virus producing cells described under 5b. comprising difference integrase mutants were used to infect NIH/3T3 cells. After transduction the viral genome is reverse transcribed. The rate of reverse transcription was studied by real-time PCR. After reverse transcription the integrase catalyses the integration of the retroviral DNA into the genome of the host cell. Only after integration the retroviral genome is expressed. The expression of the retroviral genes was analyzed by the detection of EGFP produced in the NIH3T3 cells by FACS analysis.

6a. Transduction of NIH3T3 Cells with Retroviral Particles of the Virus Producing Cells The supernatants of the virus producing cells 29GAGVPC, 29184VPC, 29203VPC, 29263VPC and 29392VPC were transferred into a 50 ml Falcon tube respectively. 1 ml of supernatant was transferred into a 1.5 ml Eppendorf tube and frozen at −20° C. for later estimation of viral load by means of real-time RT-PCR.

The collected supernatant was used to infect NIH3T3 cells: $5\times10^5$ NIH3T3 cells were seeded in 10 cm dishes one day prior infection using a medium comprising 8 ml DMEM with 5% FCS. 50–70% confluence was observed at the day of infection.

For each virus producing cell line 23 of those 10 cm dishes with NIH3T3 cells were used. For infection, the medium was removed first. Then, 2 ml of the supernatant of the virus producing cells was placed onto the cells employing a 0.45 $\mu$m filter attached to a 10 ml syringe. 2 $\mu$l of polybrene (8 $\mu$l/ml) was added immediately. All dishes were incubated at 37° C. at 5% $CO_2$ for one hour. Cells were washed twice with 10 ml phosphate-buffered saline (PBS). Then, DMEM with 5% FCS was added.

Transduced NIH3T3 cells were harvested, pelleted and frozen at the following time points: 0.5, 1.5, 2.5, 3.5, 4.5, 5.5, 25.5 and 96.5 hours (h) and then in weekly intervals post infection (p.i.). Cells were harvested in triplicates. addition to the dishes with infected cells, two 10 cm dishes were used as negative controls. Uninfected cells were harvested using 1 ml Trypsin per dish, detached cells were transferred into a 1.5 ml Eppendorf tube and centrifuged at 1600 rpm for 5 min. Supernatant was removed and the cells were frozen at −20° C.

6b. Analysis of Transduction Efficiency and EGFP Expression

FACS analysis was used to determine the expression of EGFP from 24 h p.i. onwards. Cell pellets were re-suspended in 1 ml PBS and measured in the FACSCalibur (Becton Dickinson).

Transduction efficiency was estimated by multiplex real-time PCR as described in Klein et al., Gene Ther. 7 (6): 458–63.

DNA for real-time PCR was extracted using a commercial kit (DNEASY Tissue Kit, Qiagen, Germany) according to the manufacturer's protocol. Extraction of RNA was also performed by means of commercial kits. The Viral RNA Mini Kit (Qiagen, Germany) was used for the extraction of RNA from supernatant. Cellular RNA was extracted by means of the RNeasy Mini Kit (Qiagen, Germany).

A standard for the real-time PCR was obtained by performing a dilution series of DNA of NIH3T3 cells stably infected with pLXSNEGFP (Klein et al., Gene Ther. 4: 1256–1260). This DNA was used to estimate the sensitivity of the PCR reactions. DNA was extracted using the DNeasy tissue kit (Qiagen, Germany). The DNA concentration was estimated by means of OD at 260 nm and a fourfold dilution series was obtained by dilution in PCR-grade water. The standard dilution was included in each PCR.

A multiplex real-time PCR set-up was used for the simultaneous calculation of EGFP copy number and cell number in one real-time PCR reaction. The TaqMan probes and primers were designed with Primer Express software (Perkin Elmer, USA).

The EGFP234p assay was used to calculate the number of retroviral genomes in the sample. It comprises the primers EGFP214f (5'-GCA GTG CTT CAG CCG CTA C-3') (SeqID No. 23) and EGFP309r (5'-AAG AAG ATG GTG CGC TCC TG-3') (SeqID No. 24) and the probe EGFP234p (5'-VIC-CCG ACC ACA TGA AGC AGC ACG ACT T-TAMRA-3') (SeqID No. 25). The probe EGFP234v was labeled with VIC as a reporter fluorochrome and TAMRA (6-carboxy-tetramethyl-rhodamine) as quencher. The probe was blocked at the 3' end to prevent elongation during the PCR reaction. An rDNA assay was used to calculate the total number of NIH3T3 cells in the sample. It consisted of the primers rDNA343f (5'-CCA TCG AAC GTC TGC CCT A-3') (SeqID No. 26) and rDNA409r (5'-TCA CCC GTG GTC ACC ATG-3') (SeqID No. 27) and the probe rDNA370p (5'-FAM-CGA TGG TGG TCG CCG TGC CTA-TAMRA-3') (SeqID No. 28). The probe rRNA370p was labeled with FAM (6-carboxy-fluorescein) as reporter dye and TAMRA (6-carboxy-tetramethyl-rhodamine) as a quencher.

With the primers and probes a multiplex real-time PCR was performed. 25 $\mu$l PCR reactions were used containing 3 mM $MgCl_2$, 200 nM dATP, dCTP, dGTP, 400 nM dUTP, 300 nm of each primer, 200 nM of the probe and 1.25 units of Taq DNA polymerase. The real-time PCR reactions were performed in a ABI Prism 7700 Sequence Detection System (Perkin Elmer) for 45 cycles (initial denaturation 2 min at 95° C., followed by 15 sec at 95°, 1 min at 60°).

The EGFP copy number and the cell number per sample was calculated as described by Klein et al., Gene Ther. 7 (6): 458–63. The transduction efficiency was estimated as the ratio of the EGFP copy number per cell number.

6c. Results

The calculated transduction efficiency (reflecting the amount of reverse transcribed viral DNA in the transduced cell) was estimated at different time-points after transduction using four different real-time PCRs. The amount of integrated and therefore expressed viral genomes was estimated using FACS analysis at the same time-points.

Time Course Integrase Mutants

| Cell line | Time (h) | four different real-time PCTs | | | | FACS |
|---|---|---|---|---|---|---|
| 29GAGVPC | | ml8tl | ml8rl | ml8t2 | ml8r2 | |
| | 0.00 | 0.00 | 0.00 | 0.00 | 0.07 | 0 |
| | 0.50 | 0.85 | 0.55 | 0.63 | 0.37 | 0 |
| | 1.50 | 1.07 | 0.66 | 1.75 | 1.21 | 0 |
| | 2.50 | 1.24 | 0.80 | 1.12 | 0.96 | 0.003 |
| | 3.50 | 2.48 | 2.70 | 0.92 | 1.00 | 0 |
| | 4.50 | 3.59 | 4.14 | 3.33 | 3.70 | 0 |
| | 5.50 | 2.11 | 5.35 | 2.95 | 5.85 | 0 |
| | 25.50 | 57.80 | 64.38 | 99.17 | 90.51 | 1.140 |
| | 97.50 | 7.87 | 9.81 | 10.32 | 12.40 | 6.959 |
| 29184VPC | | ml8tl | ml8rl | ml8t2 | ml8r2 | FACS |
| | 0.00 | 0.00 | 0.00 | 0.00 | 0.00 | 0 |
| | 0.50 | 0.52 | 0.57 | 0.89 | 0.64 | 0 |
| | 1.50 | 0.96 | 0.59 | 1.44 | 0.54 | 0 |
| | 2.50 | 2.12 | 1.03 | | | 0 |
| | 3.50 | 1.91 | 1.51 | 1.53 | 1.05 | 0 |
| | 4.50 | 1.46 | 0.93 | 1.43 | 0.82 | 0 |
| | 5.50 | 2.53 | 1.48 | 1.76 | 1.12 | 0 |

-continued

| Cell line | Time (h) | four different real-time PCTs | | | | FACS |
|---|---|---|---|---|---|---|
| | 25.50 | 19.84 | 18.24 | 17.41 | 13.00 | 0.001 |
| | 97.50 | 0.18 | 0.20 | 0.09 | 0.08 | 0.002 |
| 29263VPC | | ml9tl | ml9rl | ml9t2 | ml9r2 | FACS |
| | 0.00 | 0.00 | 0.00 | 0.00 | 0.00 | 0 |
| | 0.50 | 1.02 | 1.12 | 2.18 | 1.53 | 0 |
| | 1.50 | 3.16 | 1.55 | 0.77 | 0.57 | 0 |
| | 2.50 | 2.77 | 1.79 | 4.46 | 4.04 | 0 |
| | 3.50 | 3.37 | 2.56 | 3.27 | 3.33 | 0 |
| | 4.50 | 6.86 | 6.15 | 6.98 | 6.95 | 0 |
| | 5.50 | 7.65 | 8.85 | 7.70 | 10.74 | 0.004 |
| | 25.50 | 43.75 | 34.15 | 38.91 | 36.10 | 0.002 |
| | 97.50 | 0.41 | 0.95 | 0.36 | 0.48 | 0.004 |
| 29203VPC | | ml9tl | ml9rl | ml9t2 | ml9r2 | FACS |
| | 0.00 | 0.03 | 0.11 | 0.60 | 0.87 | 0 |
| | 0.50 | 0.70 | 1.00 | 1.72 | 1.70 | 0 |
| | 1.50 | 1.04 | 0.91 | 1.67 | 0.89 | 0 |
| | 2.50 | 0.26 | 0.11 | 1.78 | 0.84 | 0 |
| | 3.50 | 1.15 | 0.89 | 1.90 | 1.52 | 0 |
| | 4.50 | 2.63 | 2.16 | 1.46 | 0.92 | 0 |
| | 5.50 | 2.12 | 2.04 | 1.95 | 2.04 | 0 |
| | 25.50 | 15.95 | 45.51 | 56.93 | 59.07 | 0.001 |
| | 97.50 | 1.14 | 065 | 0.31 | 0.26 | 0.004 |

During the first 24 h after infection, the content of viral DNA of the samples infected with the retroviral-particles comprising the wild-type integrase and the mutated integrase was in the same range. Hence, wild-type and mutant virions entered the NIH/3T3 host cells with the same rate and kinetic, which demonstrates that neither the reverse transcription of the retroviral genome nor any earlier step in the retroviral life cycle is impaired by the mutation in the pol region Furthermore, 96 h post infection the amount of cells containing retroviral genomes (estimated by multiplex real-time PCR) was similar to the amount of cells expressing the transduced marker gene (estimated by FACS analysis) in the target cells, which have been transduced by wild-type virions (29GAGVPC). In contrast, 97.5 h post infection barely no EGFP expression was observed by FACS analysis of cells transduced with integrase mutants. Hence, the cells infected with the integrase mutants contained the EGFP gene but did not express it. These results correspond well with the expectations: If the integrase is inactivated by a mutation or deletion, the viral DNA produced by reverse transcription is not integrated into the host cell genome. However, since viral genes are only expressed after the integration of the viral genome into the host cell genome, no expression of genes in the retroviral genome is expected when the integrase is inactivated, i.e. in this case, no EGFP expressions is expected.

Furthermore, 97.5 h post infection, the content of viral DNA was considerably lower in the samples infected with the integrase mutants than in cells infected with the wild-type. This observation may as well be explained by an integrase deficiency of the virions with a mutated pol region: Viral DNA, which is not integrated into the genome of the host cell, is degraded by enzymes of the host cell. In contrast, if the integrase is active, the viral DNA is integrated into the host cell genome and consequently protected from degradation. Hence, the viral DNA content of cells infected with viruses with a mutated pol region decreases over time due to permanent degradation of the viral DNA.

In conclusion, the mutations in the pol region of the retroviral genome inhibit the integration into the host cell DNA, but do not affect any earlier step of the retroviral life cycle. In this case, the reverse transcribed retroviral genome is present in the transduced target cell and hence can be used for targeted integration according to the present invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A retroviral vector comprising one or more heterologous nucleic acid sequence(s) as well as at least one sequence allowing site-specific integration of said heterologous sequence(s) into a non-coding region of a genome, wherein the sequence allowing site-specific integration is an Inverted Terminal Repeat (ITR) sequence of Adeno-associated virus (AAV), and wherein the sequence(s) allowing site specific integration is inserted at the U3 region(s) and/or the U5 region(s) of the retroviral Long Terminal Repeat (LTR).

2. The retroviral vector according to claim 1, wherein the genome is a chromosome of a mammal, including human.

3. The retroviral vector according to claim 2, wherein the chromosome is human chromosome 19.

4. The retroviral vector according to claim 1, wherein at least one of the heterologous nucleic acid sequence(s) is a sequence encoding an integration-mediating protein, wherein the integration-mediating protein is an AAV Rep-protein.

5. The retroviral vector according to claim 1, wherein the sequence encoding for the integration-mediating protein is under transcriptional control of an inducible promoter.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gactccacgc gtccaggaac        20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
gaccgcggat catcgataag        20

-continued

```
<210> SEQ ID NO 3
<211> LENGTH: 24
<212> TYPE: DNA
<213> ORGANISM: Artificial Sequence
<220> FEATURE:
<223> OTHER INFORMATION: PCR Primer

<400> SEQUENCE: 3
tcacgactcc accggtccag gaac                                              24

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
gtttgaccgg ttatcatcga taag                                              24

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
acaagtcaac gccagcaagt                                                   20

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
cccattgtta gttcccaata cctgag                                            26

<210> SEQ ID NO 7
<211> LENGTH: 24
<212> TYPE: DNA
<213> ORGANISM: Artificial Sequence
<220> FEATURE:
<223> OTHER INFORMATION: PCR Primer

<400> SEQUENCE: 7
tgggaactaa caatgggcct gcct                                              24

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
cgttgaacgc gccatgtcag                                                   20

<210> SEQ ID NO 9
<211> LENGTH: 28
<212> TYPE: DNA
<213> ORGANISM: Artificial Sequence
<220> FEATURE:
<223> OTHER INFORMATION: PCR Primer
```

```
<400> SEQUENCE: 9
ggcccattgt tagttcccaa tacctgag                                    28

<210> SEQ ID NO 10
<211> LENGTH: 23
<212> TYPE: DNA
<213> ORGANISM: Artificial Sequence
<220> FEATURE:
<223> OTHER INFORMATION: PCR Primer

<400> SEQUENCE: 10
tgggaactaa caatgggccc tgc                                         23

<210> SEQ ID NO 11
<211> LENGTH: 39
<212> TYPE: DNA
<213> ORGANISM: Artificial Sequence
<220> FEATURE:
<223> OTHER INFORMATION: PCR Primer 263

<400> SEQUENCE: 11
atataggccc ccatggcctc ccctaatccc cttaattct                        39

<210> SEQ ID NO 12
<211> LENGTH: 40
<212> TYPE: DNA
<213> ORGANISM: Artificial Sequence
<220> FEATURE:
<223> OTHER INFORMATION: PCR Primer 277

<400> SEQUENCE: 12 ataggccc ccatggcctc cgctctcaaa acccttaaa                          40

<210> SEQ ID NO 13
<211> LENGTH: 39
<212> TYPE: DNA
<213> ORGANISM: Artificial Sequence
<220> FEATURE:
<223> OTHER INFORMATION: PCR Primer 289

<400> SEQUENCE: 13 ataggccc ccatggcctc ggtggaccat cctctagac                          39

<210> SEQ ID NO 14
<211> LENGTH: 39
<212> TYPE: DNA
<213> ORGANISM: Artificial Sequence
<220> FEATURE:
<223> OTHER INFORMATION: PCR Primer 306

<400> SEQUENCE: 14 ataggccc ccatggcctc ggcatcgcag cttggatac                          39

<210> SEQ ID NO 15
<211> LENGTH: 37
<212> TYPE: DNA
<213> ORGANISM: Artificial Sequence
<220> FEATURE:
<223> OTHER INFORMATION: PCR Primer 360

<400> SEQUENCE: 15 ataggccc ccatggcctc gcagcctacc aagaaca                            37

<210> SEQ ID NO 16
<211> LENGTH: 38
```

```
<212> TYPE: DNA
<213> ORGANISM: Artificial Sequence
<220> FEATURE:
<223> OTHER INFORMATION: PCR Primer 364

<400> SEQUENCE: 16
atataggccc ccatggcctc tggagacctc tggcggca                               38

<210> SEQ ID NO 17
<211> LENGTH: 38
<212> TYPE: DNA
<213> ORGANISM: Artificial Sequence
<220> FEATURE:
<223> OTHER INFORMATION: PCR Primer 371

<400> SEQUENCE: 17
atataggccc ccatggcctc ttagtccagc acgaagtc                               38

<210> SEQ ID NO 18
<211> LENGTH: 38
<212> TYPE: DNA
<213> ORGANISM: Artificial Sequence
<220> FEATURE:
<223> OTHER INFORMATION: PCR Primer 381

<400> SEQUENCE: 18
atataggccc ccatggcctc tctctccaag ctcactta                               38

<210> SEQ ID NO 19
<211> LENGTH: 37
<212> TYPE: DNA
<213> ORGANISM: Artificial Sequence
<220> FEATURE:
<223> OTHER INFORMATION: PCR Primer 392

<400> SEQUENCE: 19
atataggccc ccatggcctc gaccctgaca tgacaag                                37

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
gtcagcaacc aggtgtggaa                                                   20

<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21
gcgaagcttt ccacaggatg ccgaatcacc                                        30

<210> SEQ ID NO 22
<211> LENGTH: 30
<212> TYPE: DNA
<213> ORGANISM: Artificial Sequence
<220> FEATURE:
<223> OTHER INFORMATION: PCR Primer

<400> SEQUENCE: 22
```

-continued atagcgcgcc caagtttgca gcagagaatg                              30

<210> SEQ ID NO 23
<211> LENGTH: 19
<212> TYPE: DNA
<213> ORGANISM: Artificial Sequence
<220> FEATURE:
<223> OTHER INFORMATION: Primer EGFP214f

<400> SEQUENCE: 23
gcagtgcttc agccgctac                                          19

<210> SEQ ID NO 24
<211> LENGTH: 20
<212> TYPE: DNA
<213> ORGANISM: Artificial Sequence
<220> FEATURE:
<223> OTHER INFORMATION: Primer EGFP309r

<400> SEQUENCE: 24
aagaagatgg tgcgctcctg                                         20

<210> SEQ ID NO 25
<211> LENGTH: 25
<212> TYPE: DNA
<213> ORGANISM: Artificial Sequence
<220> FEATURE:
<223> OTHER INFORMATION: Primer EGFP234p

<400> SEQUENCE: 25
ccgaccacat gaagcagcac gactt                                   25

<210> SEQ ID NO 26
<211> LENGTH: 19
<212> TYPE: DNA
<213> ORGANISM: Artificial Sequence
<220> FEATURE:
<223> OTHER INFORMATION: Primer rDNA343f

<400> SEQUENCE: 26
ccatcgaacg tctgcccta                                          19

<210> SEQ ID NO 27
<211> LENGTH: 18
<212> TYPE: DNA
<213> ORGANISM: Artificial Sequence
<220> FEATURE:
<223> OTHER INFORMATION: Primer rDNA409r

<400> SEQUENCE: 27
tcacccgtgg tcaccatg                                           18

<210> SEQ ID NO 28
<211> LENGTH: 21
<212> TYPE: DNA
<213> ORGANISM: Artificial Sequence
<220> FEATURE:
<223> OTHER INFORMATION: Probe rDNA370p

<400> SEQUENCE: 28
cgatggtggt cgccgtgcct a                                       21